US010786305B2

(12) United States Patent
Mahvi et al.

(10) Patent No.: US 10,786,305 B2
(45) Date of Patent: Sep. 29, 2020

(54) RADIOFREQUENCY PROBE FOR CIRCUMFERENTIAL ABLATION OF A HOLLOW CAVITY

(71) Applicant: Northwestern University, Evanston, IL (US)

(72) Inventors: David M. Mahvi, Chicago, IL (US); Daniel P. McCarthy, Chicago, IL (US); Tyler R. Wanke, Chicago, IL (US); Brian J. Robillard, Chicago, IL (US)

(73) Assignee: Northwestern University, Evanston, IL (US)

( * ) Notice: Subject to any disclaimer, the term of this patent is extended or adjusted under 35 U.S.C. 154(b) by 1421 days.

(21) Appl. No.: 13/954,265

(22) Filed: Jul. 30, 2013

(65) Prior Publication Data
US 2014/0031810 A1 Jan. 30, 2014

Related U.S. Application Data

(60) Provisional application No. 61/677,205, filed on Jul. 30, 2012.

(51) Int. Cl.
*A61B 18/18* (2006.01)
*A61B 18/14* (2006.01)
*A61B 18/00* (2006.01)

(52) U.S. Cl.
CPC .......... *A61B 18/18* (2013.01); *A61B 18/1492* (2013.01); *A61B 2018/0016* (2013.01);
(Continued)

(58) Field of Classification Search
CPC .. A61B 2018/0022; A61B 2018/00232; A61B 2018/00267; A61B 2018/00238
See application file for complete search history.

(56) References Cited

U.S. PATENT DOCUMENTS 4,979,948 A 12/1990 Geddes et al.
5,471,982 A 12/1995 Edwards et al.
(Continued)

FOREIGN PATENT DOCUMENTS

DE 102010032932 A1 2/2012
WO WO-0051683 A1 9/2000

OTHER PUBLICATIONS

International Searching Authority, International Search Report and Written Opinion for PCT/US2013/052703, dated Nov. 29, 2013, 2 pgs.
(Continued)

*Primary Examiner* — Michael F Peffley
*Assistant Examiner* — Bo Ouyang
(74) *Attorney, Agent, or Firm* — Wilson Sonsini Goodrich & Rosati

(57) ABSTRACT

A probe for ablating tissue of a body cavity includes a shaft, an inflatable balloon connected to the shaft, and an electrode structure on or surrounding the balloon. The balloon expands within the body cavity to place the electrode structure in contact with the tissues in the body cavity. Additional electrodes, which are housed within the balloon during insertion into the cavity, can be extended outwardly from the balloon to penetrate the tissues in the body cavity. The electrode structure and the additional electrodes are adapted to transmit electrical energy to tissue of the body cavity in order to ablate the tissues up to a predetermined depth.

10 Claims, 4 Drawing Sheets

(52) U.S. Cl.
CPC ............... *A61B 2018/0022* (2013.01); *A61B 2018/00226* (2013.01); *A61B 2018/00267* (2013.01); *A61B 2018/00333* (2013.01); *A61B 2018/1465* (2013.01); *A61B 2018/1467* (2013.01); *A61B 2018/1475* (2013.01)

(56) References Cited

U.S. PATENT DOCUMENTS

| | | | |
|---|---|---|---|
| 5,562,720 A | 10/1996 | Stern et al. | |
| 5,672,153 A * | 9/1997 | Lax | A61B 10/0233 604/22 |
| 5,713,942 A | 2/1998 | Stern et al. | |
| 5,772,590 A | 6/1998 | Webster, Jr. | |
| 5,871,483 A | 2/1999 | Jackson et al. | |
| 5,928,229 A | 7/1999 | Gough et al. | |
| 6,009,877 A * | 1/2000 | Edwards | 128/898 |
| 6,036,689 A * | 3/2000 | Tu et al. | 606/41 |
| 6,123,718 A | 9/2000 | Tu et al. | |
| 6,142,993 A | 11/2000 | Whayne et al. | |
| 6,258,087 B1 | 7/2001 | Edwards et al. | |
| 6,379,353 B1 | 4/2002 | Nichols | |
| 6,491,710 B2 | 12/2002 | Satake | |
| 6,503,247 B2 | 1/2003 | Swartz et al. | |
| 6,551,310 B1 | 4/2003 | Ganz et al. | |
| 6,692,466 B1 * | 2/2004 | Chow | A61M 25/0084 604/164.01 |
| 6,826,421 B1 | 11/2004 | Beatty et al. | |
| 7,150,745 B2 | 12/2006 | Stern et al. | |
| 7,344,535 B2 | 3/2008 | Stern et al. | |
| 7,371,231 B2 | 5/2008 | Rioux et al. | |
| 7,556,628 B2 | 7/2009 | Utley et al. | |
| 7,632,268 B2 | 12/2009 | Edwards et al. | |
| 7,769,432 B2 | 8/2010 | Klimberg et al. | |
| 7,828,793 B2 | 11/2010 | Thompson et al. | |
| 7,959,631 B2 * | 6/2011 | DiCarlo | A61B 18/1477 606/41 |
| 8,388,573 B1 * | 3/2013 | Cox | 604/103.01 |
| 2002/0087208 A1 * | 7/2002 | Koblish et al. | 607/113 |
| 2002/0115992 A1 * | 8/2002 | Utley et al. | 606/41 |
| 2004/0087936 A1 | 5/2004 | Stern et al. | |
| 2005/0154386 A1 * | 7/2005 | West | A61B 18/1492 606/41 |
| 2008/0004534 A1 * | 1/2008 | Gelbart et al. | 600/508 |
| 2009/0292177 A1 * | 11/2009 | Eggers | A61B 10/0266 600/219 |
| 2010/0114087 A1 * | 5/2010 | Edwards | A61B 18/1477 606/33 |
| 2011/0257646 A1 * | 10/2011 | Utley et al. | 606/33 |
| 2012/0109250 A1 | 5/2012 | Cates et al. | |
| 2013/0158536 A1 * | 6/2013 | Bloom | 606/33 |

OTHER PUBLICATIONS

European search report dated Mar. 16, 2016 for EP Application No. 13825361.2.

* cited by examiner

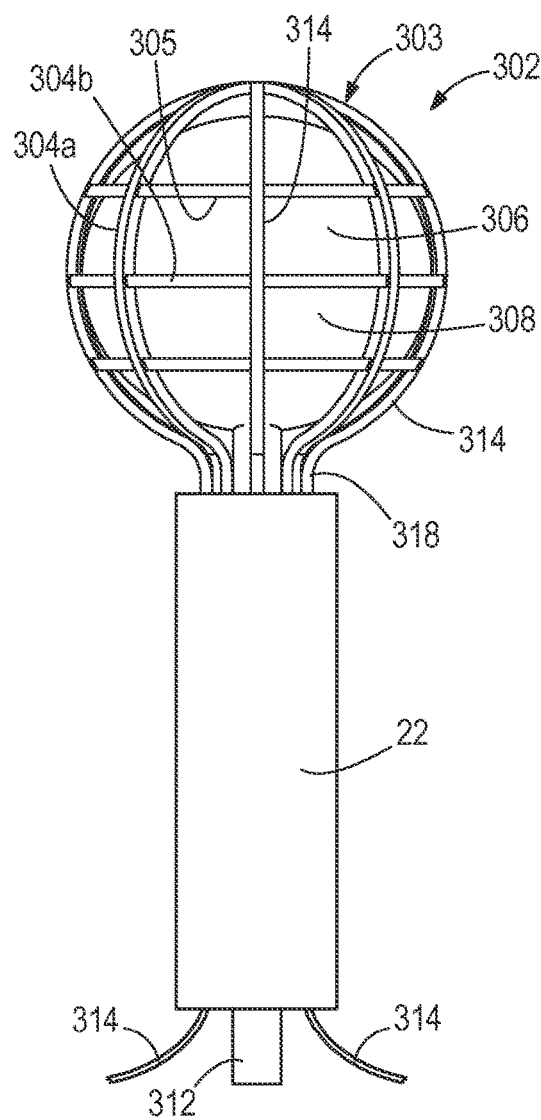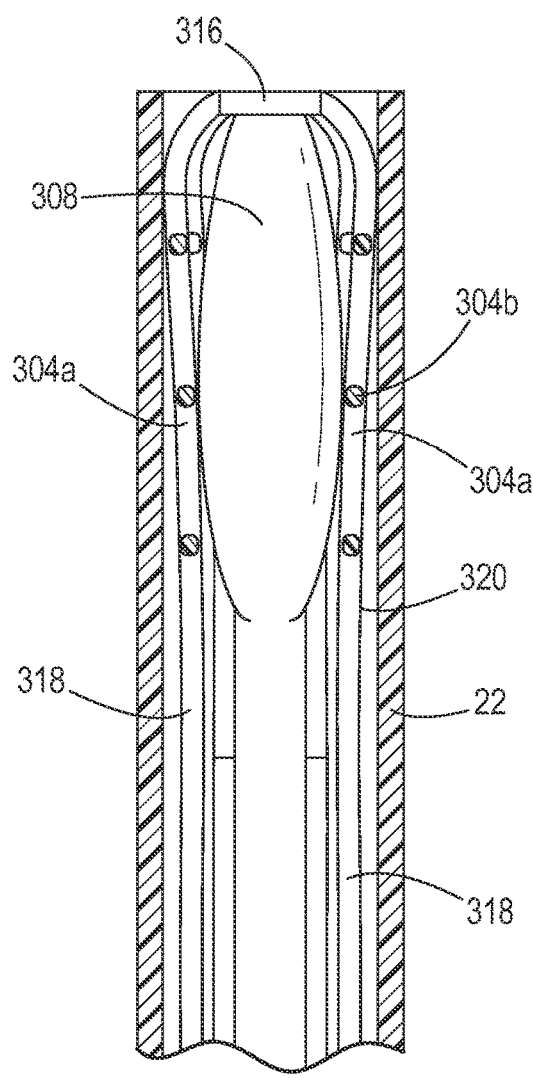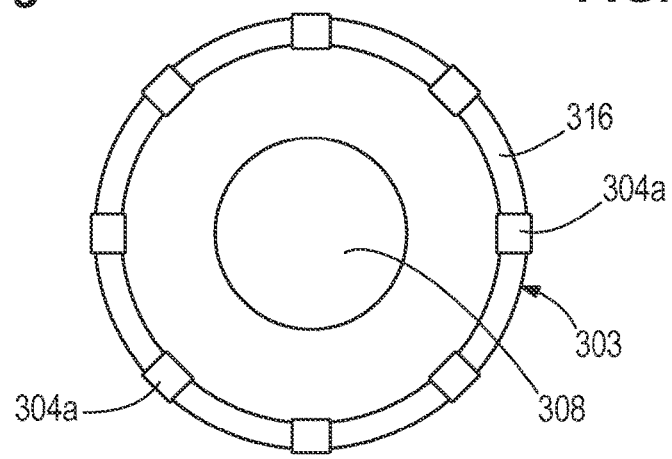
FIG. 3
FIG. 5
FIG. 4

RADIOFREQUENCY PROBE FOR CIRCUMFERENTIAL ABLATION OF A HOLLOW CAVITY

This application claims the domestic priority of U.S. provisional application Ser. No. 61/677,205 filed on Jul. 30, 2012, the contents of which are incorporated herein by reference in its entirety.

BACKGROUND

Radiofrequency ablation (RFA) is a medical procedure used to ablate living tissues. RFA is also used to control bleeding in internal organs.

One advantage of a radiofrequency (RF) current over previously used low frequency alternating currents (AC) or pulses of direct currents (DC) is that it does not directly stimulate nerves and can therefore often be used without the need for local or general anesthesia. For cancerous breast tumors, RFA has been used as a nonsurgical, localized treatment that kills tumor cells with heat, while sparing the healthy breast tissue. Because of the localized nature of this treatment, RFA does not have any systemic side effects. RFA can be performed without affecting a patient's overall health so as to resume his/her usual activities in a few days.

Moreover, treatment of early stage breast cancer typically involves a combination of lumpectomy and whole breast irradiation (WBI). Such ionizing radiation results in short and long-term complications affecting the skin, lungs, and heart. Therefore, up to thirty percent (30%) of women who undergo lumpectomy do not complete WBI. The burden of weeks of daily WBI drives some women to choose mastectomy instead of lumpectomy, and is one reason so many women prematurely discontinue their radiation treatment—the full time course of which is needed to achieve safe results.

Experimental data suggest that improved benefits can be achieved by delivering radiation to the breast tissue immediately surrounding the lumpectomy site. However, these accelerated partial breast irradiation (APBI) techniques still require a few days of treatment, and frequently involve a separate procedure for catheter implantation.

Conventionally, interventional radiologists have used imaging to guide a small needle through the skin into the tumor. From the tip of the needle, radiofrequency energy is transmitted into the tumor, where it produces heat and kills the tumor. A similar technique can be used to minimize recurrence of the tumor in instances when the breast tumor has already been removed surgically via a lumpectomy. However, this needle and other commercially available RFA probes are not configured for use in the lumpectomy cavity, and may contribute to longer treatment times or inconsistent energy delivery due to non-specific shape and/or poor usability.

As such, there is a need for a device that can be used to deliver non-ionizing radiation, such as RFA, to deliver precise levels of specifically targeted energy to the tissue immediately surrounding the site of a surgically-removed tumor in order to minimize recurrence of the tumor.

SUMMARY

Disclosed herein is a radiofrequency probe for circumferential ablation of a hollow cavity. A probe for ablating tissue of a body cavity includes a shaft, an inflatable balloon connected to the shaft, and an electrode structure on or surrounding the balloon. The balloon expands within the body cavity to place the electrode structure in contact with the tissues in the body cavity. Additional electrodes, which are housed within the balloon during insertion into the cavity, can be extended outwardly from the balloon to penetrate the tissues in the body cavity. The electrode structure and the additional electrodes are adapted to transmit electrical energy to tissue of the body cavity in order to ablate the tissues up to a predetermined depth.

These as well as other aspects, advantages, and alternatives will become apparent to those of ordinary skill in the art by reading the following detailed description, with reference where appropriate to the accompanying drawings. Further, it should be understood that this summary section and the rest of this document are intended to discuss the provided disclosure by way of example only and not by way of limitation.

BRIEF DESCRIPTION OF THE DRAWINGS

FIG. 3 is a side elevation view of a third embodiment of a radiofrequency probe and inserted into a catheter;

FIG. 4 is an end elevation view of the radiofrequency probe shown in FIG. 3 without the catheter;

FIG. 5 is a cross-sectional view of the radiofrequency probe shown in FIG. 3 and inserted into a catheter;

Figure 1:
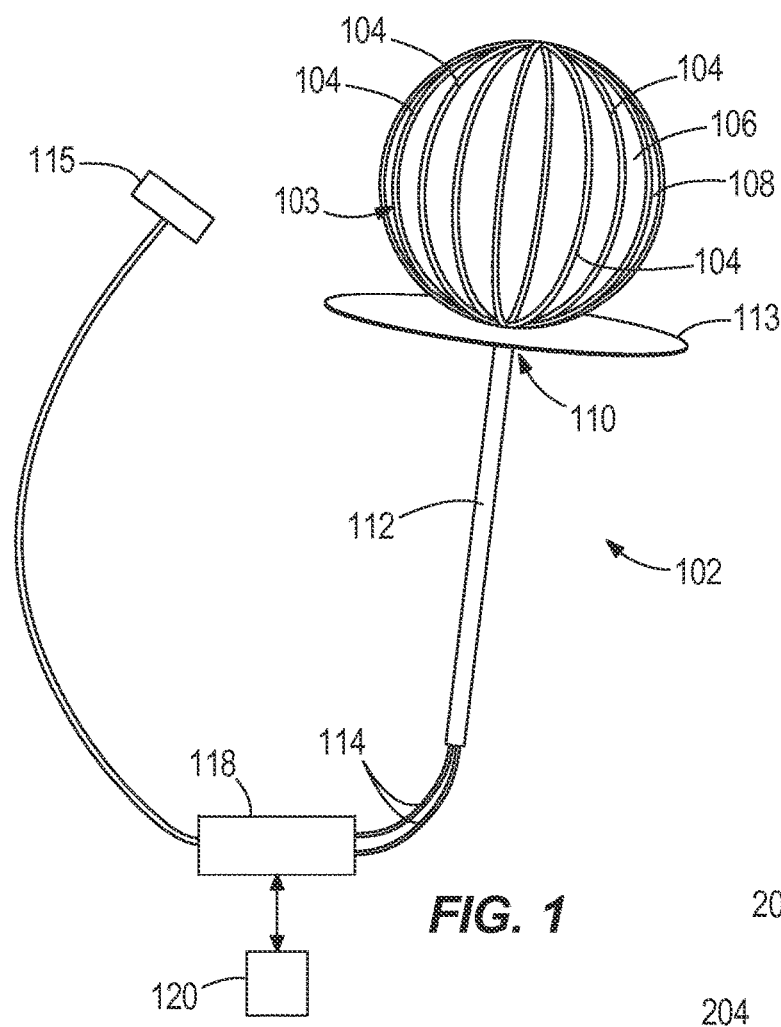
FIG. 1 is a side elevation view of a first embodiment of a radiofrequency probe.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description and figures are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

As stated above, treatment of early stage breast cancer may involve a combination of lumpectomy and whole breast irradiation (WBI). Treatment data suggest that similar benefits can be achieved by delivering radiation only to the breast tissue immediately surrounding the lumpectomy site. However, these accelerated partial breast irradiation (APBI) techniques still require five or more days of treatment, and frequently involve a separate procedure for catheter implantation. Moreover, commercially available radiofrequency ablation (RFA) probes are not configured for use in surgically-created cavities, and typically require multiple passes in order to ablate an entire surface of a wall of a cavity.

Accordingly, exemplary embodiments of RFA probes are configured for use in cavities produced surgically, such as lumpectomy cavities, to ablate in a substantially rapid and consistent manner a margin of tissue along the entire cavity wall in a single pass or treatment. These RFA probe embodiments have the potential to achieve desirable treatment outcomes in a faster, more convenient manner. These RFA probe embodiments are configured to be used during an initial surgical operation, to have built-in protection against inadvertent skin damage, and to reduce inter-operator variability that is common in currently available probes.

An exemplary embodiment of an RFA probe includes electrodes arranged on an external surface of a balloon, for use after the surgery is completed and prior to closing a surgical incision. The balloon, while in a deflated state, can be introduced into the surgical cavity through the incision, and can be inflated until it fills the cavity, thus bringing the electrodes in direct physical contact with an inner surface of the surgical cavity. A size of the balloon can be determined based on the size of the cavity.

In one embodiment, the RFA probe, which includes electrodes distributed on the external surface of the balloon, is coupled to a generator that deploys alternating current through the electrodes, which may cause agitation of ions in the cavity tissue, resulting in thermal ablation with coagulative necrosis to a predetermined depth of the cavity tissue. Additionally, the RFA probe may include an insulating proximal cuff in order to protect the skin from thermal damage.

Now referring to FIG. 1, an embodiment of a RFA probe 102 having an electrode structure 103 formed of linear electrodes 104 arranged like meridians of an Earth globe on an external surface 106 of an inflatable balloon 108 is shown. The RFA probe 102 includes a flexible shaft 112 carrying inflatable balloon 108 at a distal end 110 of the shaft 112. Shaft 112 is configured to contain internally an inflation channel and one or more signal wires 114 connected to electrode structure 103.

The purpose of electrode structure 103 is to transmit ablation energy. RFA probe 102 further includes an insulating cuff or protective shield 113 at one end of inflatable balloon 108 that is adjacent to distal end 110 of the shaft 112.

The electrode structure 103 is configured to serve as a transmitter of energy that ablates body tissue. Electrode structure 103 is configured to adapt to a range of geometries, from collapsed to expanded, that inflatable balloon 108 assumes.

Electrode structure 103 is electrically coupled to signal wires 114, which extend from the electrodes 104, through the shaft 112, and are in turn electrically coupled to an RF generator 118 which allows control of several electrical parameters (frequency, wattage, etc.). Moreover, RFA probe 102 includes a separate grounding pad 115 running from a patient to RF generator 118 to complete the electrical circuit.

A controller or controlling unit 120 is coupled to RF generator 118 as a separate interface box. Alternatively, controlling unit 120 may be integral to RF generator 118. Controlling unit 120 is configured to control the delivery of radio frequency ablation energy to electrode structure 103 according to predetermined ablation criteria.

In one embodiment, RFA probe 102 is configured for ablating internal tissue of a hollow cavity 20, which may be surgically-formed or may be of an organ having a natural internal cavity, such as a heart, an esophagus, an intestine, a bladder, and a uterus. In such environment, a surgeon or physician may move or insert the shaft 112 through a body incision or through an artery, while the inflatable balloon 108, carrying electrode structure 103, is in its low profile geometry. Once inside the cavity 20, the balloon 108 is enlarged into its expanded geometry so that the electrodes 104 are placed into contact with the internal surface of the cavity 20. Radio frequency energy is conveyed from RF generator 118 to the electrodes 104, as governed by controlling unit 120, which in turn expose the radio frequency energy to the internal tissue of the cavity 20. The expanded geometry of inflatable balloon 108 enhances the energy transmission characteristics of electrode structure 103, which once in contact with the internal tissue of the cavity 20, is able to ablate the internal tissue of the cavity 20 to a predetermined depth, such as a depth of 1 to 2 centimeters, which can substantially minimize recurrence rates of the removed tumor.

Figure 2:
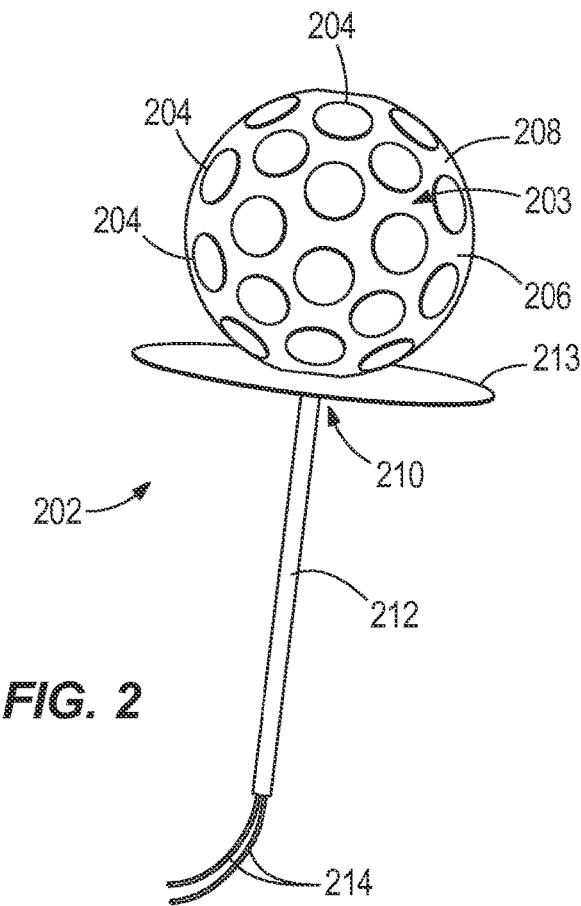
FIG. 2 is a side elevation view of a second embodiment of a radiofrequency probe.

FIG. 2 provides an alternative to the linear electrodes 104 of the embodiment of FIG. 1. In RFA probe 202, the electrode structure 203 comprises flat-plate electrodes 204 located on an external surface 206 of an inflatable balloon 208. Electrode structure 203 includes electrical wiring (not shown), located internally to balloon 208, for electrically connecting flat-plate electrodes 204 to electrical wires 214, carried within a shaft 212, which are in turn connected to an RF generator (not shown) which allows control of several electrical parameters (frequency, wattage, etc.). RFA probe 202 further includes an insulating cuff or protective shield 213 at one end of inflatable balloon 208 that is adjacent to distal end 210 of shaft 212.

As shown in FIG. 2, flat-plate electrodes 204 may have a substantially circular shape or geometry. Alternatively, flat-plate electrodes 204 may have any desirable shape, such a triangular, oval, rectangular, or square shape. Moreover, all of flat-plated electrodes 204 need not have the same shape.

Similar to electrode structure 103 of FIG. 1, electrode structure 203 is configured to serve as a transmitter of RF energy that ablates internal tissue of a hollow cavity, which may be surgically-formed or may be of an organ having a natural internal cavity as discussed hereinabove. In such environment, a surgeon or physician may move or insert shaft 212 through a body incision or through an artery, while the inflatable balloon 208, carrying electrode structure 203, is in its low profile geometry. Once inside the cavity, inflatable balloon 208 is enlarged into its expanded geometry so that flat-plate electrodes 204 are placed into contact with internal tissue of the cavity. The expanded geometry of inflatable balloon 208 enhances the energy transmission characteristics of flat-plate electrodes 204, which once in contact with the cavity's internal tissue, are able to ablate the cavity's internal tissue to a predetermined depth, such as a depth of 1 to 2 centimeters, which can substantially minimize recurrence rates of the removed tumor.

In each embodiment, the inflatable balloon 108, 208 is made of a non-conducting expandable material, such as a non-conducting elastomer, for example, polyvinyl chloride, silicone rubber, polyester, nylon, and/or polyethylene. Balloon 108, 208 is flexible to assume the expanded geometry as a result of an introduction of a gas or fluid, such as such as air or saline, into its interior at a predetermined volume and pressure, and to assume a collapsed geometry as a result of a removal of the interior gas or fluid volume and pressure. Alternatively, inflatable balloon 108, 208 may include any internal mechanism configured to expand or collapse it as desired. The balloon 108, 208 in its expanded condition preferably has an outer diameter of 1 cm to greater than 5 cm. The material of inflatable balloon 108, 208 is configured to be biocompatible and to withstand high temperatures generated by radiofrequency energy provided by RF generator 118. Inflatable balloon 108, 208 can be configured to expand to a substantially spherical and symmetric geometry. Alternatively, inflatable balloon 108 can be configured to expand to non-spherical and/or non-symmetric geometries.

Now referring to FIGS. 3-5, an embodiment of a RFA probe 302 having an electrode structure 303 around an external surface 306 of one or more inflatable balloons 308 is shown. The electrode structure 303 is separate from the balloon(s) 308. The RFA probe 302 includes a flexible shaft 312 carrying the inflatable balloon(s) 308 at its distal end 310. Shaft 312 is configured to contain internally an inflation channel for the balloon(s) 308.

The electrode structure 303 includes two sets of electrodes 304a, 304b. Each electrode 304a has a first curved portion 314 which is arranged as meridians, and each electrode 304b is curved and is arranged as transverse struts connecting adjacent ones of the first curved portions 314, thereby forming a cage or mesh structure. As a result, a plurality of apertures 305 are provided between the curved portions 314 and the electrodes 304b. At the distal end of the electrode structure 303, the curved portions 314 join together at a ring 316. The ring 316 may be shaped as a circle, hexagon, octagon or other pattern to connect the ends of the curved portions 314 together to optimize electrode spacing. Alternatively, electrode structure 303 may have any other desirable electrode arrangement that generally encircles the balloon(s) 308. The electrode structure 303 is preferably constructed with enough rigidity to maintain its expanded geometry even after the balloon(s) 308 is deflated and removed from the cavity 20 back into the central channel of the shaft 312.

Each electrode 304a has a second linear portion 318 which surrounds the shaft 312 and extends downwardly along the shaft 312. The signal wires 314 extend therefrom. An insulative sheath 320 encircles the linear portions 318. The wires 314 electrically connect electrode structure 303 to an RF generator (not shown) which allows control of several electrical parameters (frequency, wattage, etc.). Alternatively, the electrode structure 303 (eliminating second portions 318) can be attached to the end of the shaft 312, with one or more signal wires 314 extending through the shaft 312 and connected to electrode structure 303.

The electrode structure 303 and the balloon(s) 308 in their collapsed conditions are inserted into the cavity 20 by a surgeon or physician. The ring 316 "bottoms" out on the far surface of the cavity 20 which indicates to the surgeon or physician that the probe 302 is fully inserted. Thereafter, balloon(s) 308 is inflated into its expanded geometry thereby expanding electrode structure 303 to bring it in contact with internal tissue of the cavity 20. The electrode structure 303 is preferably expanded by inflation of the balloon(s) 308, however, the electrode structure 303 can also be expanded via mechanical mechanisms (e.g. spring, screw—"it is understood that the device may potentially expand/collapse the distal end of the device without the aid of a balloon while the overall design remains within the general scope of the images presented. For example, the expand/collapse mechanism might otherwise be driven by intrinsic elastic properties of the materials or by a spring, screw, automatic/manual push/pull, or other force-generating mechanism in place of the inflatable balloon."). After expansion of the electrode structure 303, the balloon(s) 308 is preferably deflated and may be removed. If the balloon(s) 308 is used, removal of the balloon(s) 308 is useful for several reasons: it allows the tissue to drape around the electrode structure 303 (i.e. by falling through the apertures 305 of the electrode structure 303), and improves ability for drainage of liquefied fat, steam, etc. created by high ablation temperatures.

Figure 6:
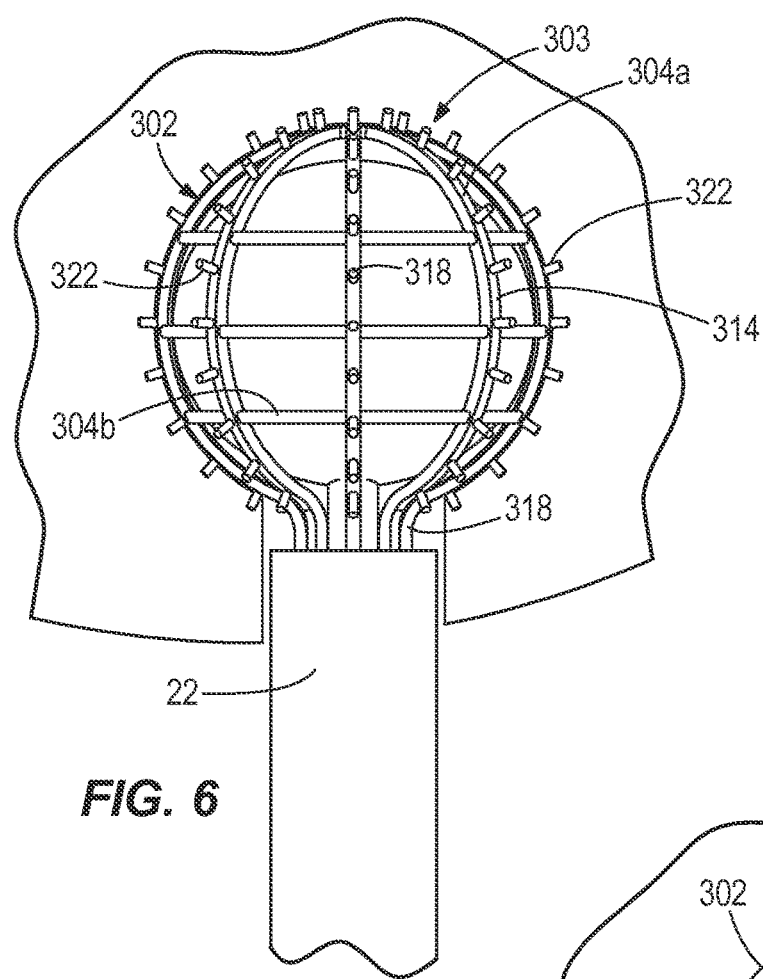
FIG. 6 is a cross-sectional view of the modified embodiment of the radiofrequency probe shown in FIG. 4, inserted through a catheter, shown inserted into a cavity in an expanded condition.
Figure 7:
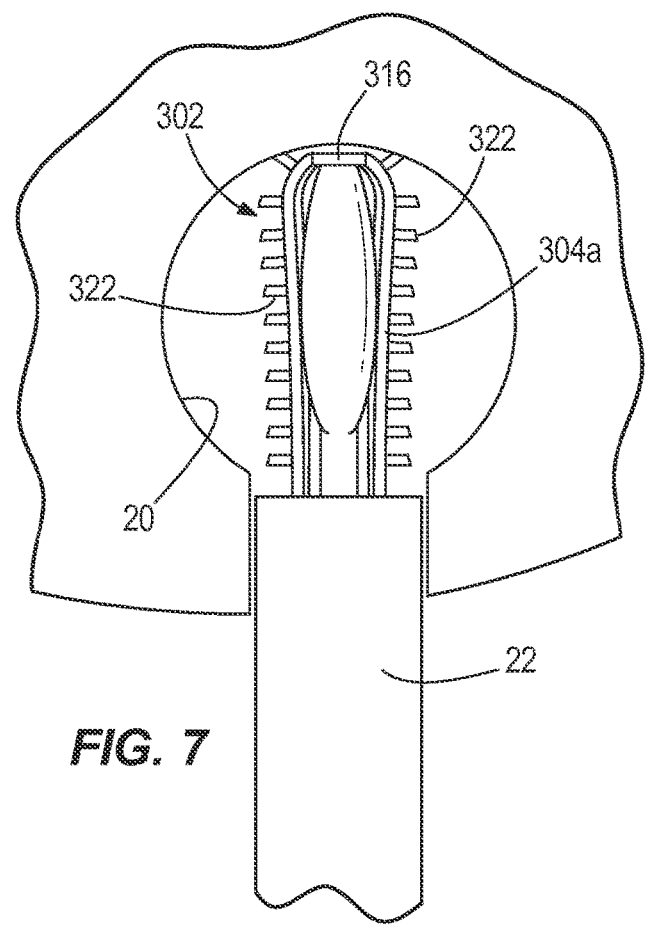
FIG. 7 is a side elevation view of a modified embodiment of a radiofrequency probe, and inserted through a catheter, and shown inserted into a cavity in a collapsed condition.
Figure 8:
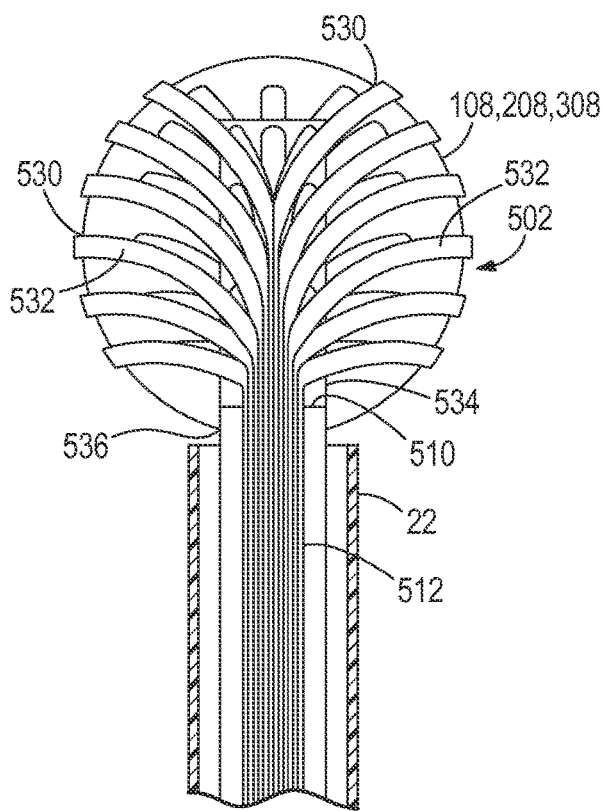
FIG. 8 is a cross-sectional view of another modified embodiment of a radiofrequency probe, shown inserted through a catheter and in expanded condition, without the electrodes mounted therein.
Figure 10:
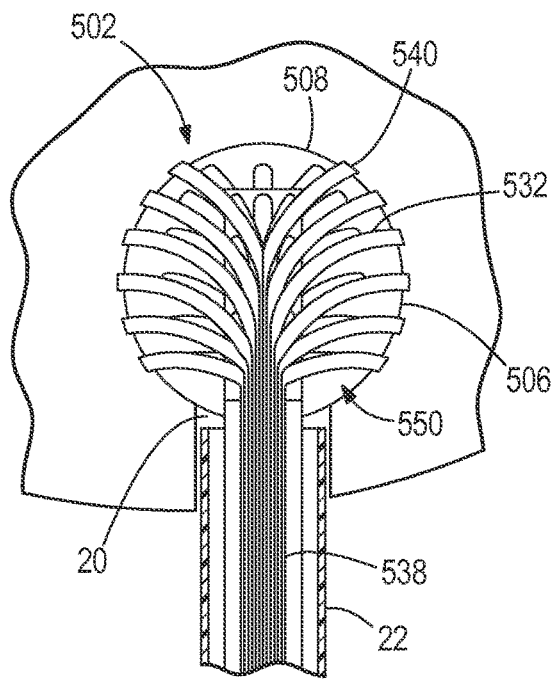
FIG. 10 is a cross-sectional view of the modified embodiment of the radiofrequency probe of FIG. 8 shown in expanded condition with electrodes present although not advanced, altogether inserted into a cavity.
Figure 9:
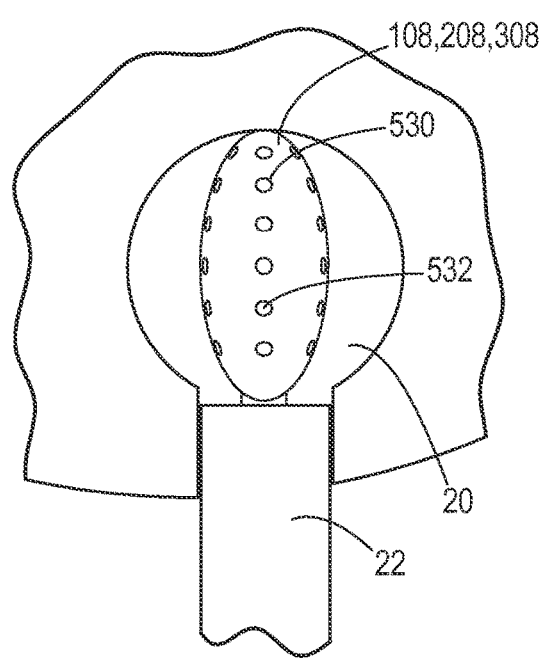
FIG. 9 is a side elevation view of the modified embodiment of the radiofrequency probe of FIG. 8 shown in partially collapsed condition without electrodes and inserted into a cavity via a catheter.
Figure 11:
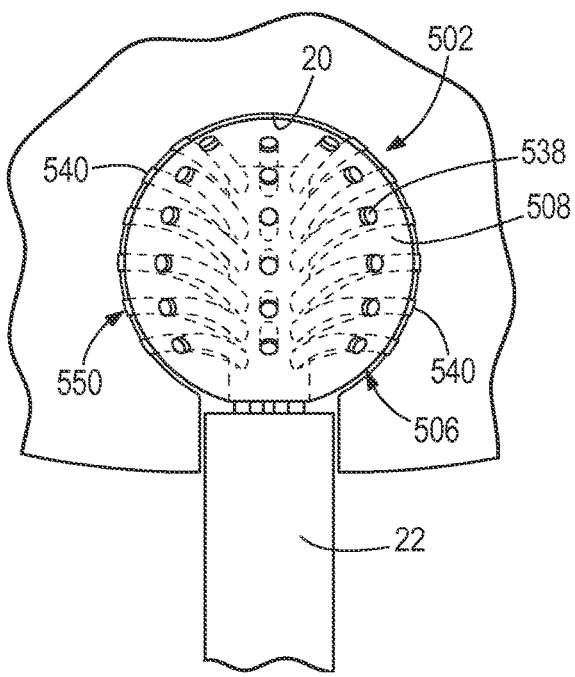
FIG. 11 is a side elevation view of the modified embodiment of the radiofrequency probe of FIG. 8 shown in expanded condition with electrodes present and advanced and inserted into a cavity.

FIGS. 6 and 7 show a modification that can be made to the RFA probe 302 of FIGS. 3-5. In this modification, the RFA probe 302 has a plurality of spaced apart protrusions 322 extending outwardly from the first curved portion 314 of the electrodes 304a as pictured but could also form part of 304b. The protrusions 322 may be integrally formed with the first curved portion 314 of the electrodes 304a, or can be formed as separate members that are spring-biased outwardly. The protrusions 322 form part of the electrodes 304a. These small protrusions 322 can also be provided on the flat-plate electrodes 204 of electrode structure 203 of FIG. 2. When the balloon/balloons 208, 308 is inflated to place the electrode structure 203, 303 into contact with the tissues of the cavity, the protrusions 322 penetrate into the surrounding internal tissue of the cavity 20 to affect contact between the electrodes 304a and tissue and potentially to provide additional depth of ablation. In order to facilitate tissue penetration, the protrusions 322 may have distal sharpness and strength to penetrate to a predetermined depth of the cavity tissue.

The balloon(s) 308 is preferably formed of a non-conducting expandable material, such as a non-conducting elastomer, for example, polyvinyl chloride, silicone rubber, polyester, nylon, and/or polyethylene. The balloon(s) 308 in its expanded condition preferably has an outer diameter of 1 cm to greater than 5 cm. Balloons of different sizes can be inserted/removed from shaft. Inflation is achieved by injection of a gas or fluid, such as air or saline into the balloon(s) 308 at a predetermined volume and pressure. Multiple inflations with different sized balloons 308 at different positions along the exposed electrode structure 303 enables creation of different geometries (i.e. large balloon distally combined followed by small balloon proximally creates a tapered ellipsoid), allowing the electrode structure 303 to be tailored to the shape of the cavity 20.

The electrode structure 303 can be formed of stainless steel, nickel/titanium alloys, copper/zinc alloys, nickel/aluminum alloys, gold, silver, and/or platinum. The electrode structure may be made of solid conductive material or even hollowed rod/wires capable of carrying fluid for purpose of heat transfer. The electrode structure 303 may have an outer diameter in an expanded condition of 1 cm to greater than 5 cm depending upon the clinical use. The electrode structure 303 may have an outer diameter in the collapsed condition of 0.5 cm to 3 cm depending upon the clinical use. The electrode structure 303 may have a length (proximal to distal) of 1 cm to greater than 5 cm depending upon the clinical use.

Now referring to FIGS. 8-11, an embodiment of a RFA probe 502 is shown. The RFA probe 502 includes an inflatable balloon 508 mounted at the distal end 510 of the shaft 512 and having an electrode structure 550 housed within the balloon 508. The purpose of electrode structure 550 is to transmit ablation energy to the tissues in the body cavity 20. Shaft 512 is configured to contain internally an inflation channel for inflation of the balloon 508. The electrode structure 550 is provided within the internal cavity of the balloon 508 and extends through the shaft 512. The balloon 508 has a plurality of spaced-apart apertures 530 provided therethrough. Each aperture 530 is sealed to the electrode structure 550.

The electrode structure 550 includes a plurality of tubes 532, with respective ones of the tubes 532 sealed at their distal ends to the respective apertures 530. The tubes 532 form passages within and through the internal cavity of the balloon 508. A closed end central shaft 534 is provided within the internal cavity of the balloon 508 and the open end 536 of the central shaft 534 is sealed to the balloon 508. The tubes 532 extend through apertures in the central shaft 534 and extend outwardly therefrom. The tubes 532 extend through the open end 536 of the central shaft 534 and through shaft 512 (the shaft 512 may be eliminated if desired). The tubes 532 and central shaft 534 may be formed of such as but not limited to silicone, Dacron, ethylene vinyl acetate (EVA), polyimide, polypropylene, Ultem, ceramic, or ABS-type plastics or a softer material, such as polyvinyl chloride, silicone rubber, polyester, nylon, and polyethylene. The tubes 532 and associated balloon 508 can collapse or expand.

The electrode structure 550 further includes a plurality of electrodes 538, with respective ones of the electrodes 538 housed in the passage of respective ones of the tubes 532. The electrodes 538 can be advanced along the tube 532 until a distal end 540 of each electrode 534 extends outwardly from the external surface 506 of the balloon 508 or can be retracted into its associated shaft 540 such that the distal end 540 is inside the associated tube 532. This can be effected by a user grasping the proximal ends of the electrodes 534 and pushing or pulling the proximal ends, or by a semi-automated method such as but not limited to a spring, screw, air, or fluid powered mechanism that can advance the electrodes 534. When the electrodes 540 are advanced along the tubes 532, the distal ends 540 extend generally radially outwardly from the external surface 506 of the balloon 508 after inflation, and the distal ends 540 penetrate into the surrounding internal tissue of a cavity 20 ensure contact between the electrodes 540 and tissue and potentially to provide additional depth of ablation. In order to facilitate tissue penetration, the electrodes 540 may have distal sharpness and strength to penetrate to a predetermined depth of the cavity tissue. With the RFA probe 502, the balloon 508 can be deflated and the electrodes structure 550 will maintain penetration of the tissues.

Housing the electrodes 538 within the balloon 508 during insertion protects the electrodes 538 and human tissue from unnecessary damage during use, while affecting safe and proper placement of the electrodes 538 into the unique contours of the cavity 20. Such ability to penetrate the tissue at multiple sites within the wall of the cavity 20 is important in that it can affect consistent contact of the electrodes 538 with the tissue. That is, by waiting to deploy the electrodes 538 until after the cavity 20 is form-fitted with the inflated balloon 508, the chance that the electrodes 538 might be damaged during inflation is lowered, and the chance of undue damage to healthy tissue by electrodes is lowered. Waiting to deploy the electrodes 538 ensures that the probe 502 is properly positioned and distributed for even/optimal ablation; externally fixed electrodes could pre-maturely penetrate and lodge into the irregularly-shaped walls of the cavity and therefore deliver energy in a non-even, improperly distributed pattern, potentially leaving marginal cancer-containing tissue un-ablated and prone to recurrence.

In each embodiment, and as shown and described in the first embodiment of the RFA probe 102, electrode structure 103, 203, 303, 550 is electrically coupled to signal wires, which extend from the electrode structure 103, 203, 303, 550, and are in turn electrically coupled to an RF generator which allows control of several electrical parameters (frequency, wattage, etc.). Moreover, the RFA probe 102, 202, 302, 5050 includes a separate grounding pad running from a patient to RF generator to complete the electrical circuit. A controller or controlling unit is coupled to RF generator as a separate interface box. Alternatively, controlling unit may be integral to RF generator. Controlling unit is configured to control the delivery of radio frequency ablation energy to electrode structure 103, 203, 303, 550 according to predetermined ablation criteria.

Any of the embodiments of FIGS. 1-7 can be modified to include electrode structure 550. When modified, the apertures 530 do not overlap the electrode structures 103, 203, 303.

While the insulating cuff or protective shield 113, 213 is not shown in the embodiments shown in FIGS. 3-11, it is to be understood that the insulating cuff or protective shield 113, 213 can be used in these embodiments. While the type of ablation energy used in any of the foregoing embodiments can vary, the electrode structure 103, 203, 303, 550 serves to transmit radio frequency (RF) electromagnetic energy.

The RFA probe 102, 202, 302, 502 may be inserted into and/or fastened to a catheter shaft 22 in a collapsed condition for introduction into the cavity 20. Once the catheter shaft 22 is properly inserted into the cavity 20 by the surgeon, the RFA probe 102, 202, 302, 502 is introduced into the proximal end of the catheter shaft 22 and advanced through the catheter shaft 22 until the distal end of the RFA probe 102, 202, 302, 502 extends from the distal end of the catheter shaft 22 and into the cavity 20. Once the balloon/balloons 108, 208, 308, 508 and electrode structure 103, 203, 303, 550 are extended outwardly from the distal end of the catheter shaft 22, the balloon/balloons 108, 208, 308, 508 is inflated to place the electrode structure 103, 203, 303, 550 into contact with the tissues of the cavity as described herein. If using the embodiments of FIGS. 6-7 and 8-11, the protrusions 322/electrodes 538 then penetrate into the surrounding internal tissue of the cavity 20 to affect contact between the electrodes 304a and tissue and potentially to provide additional depth of ablation. In order to facilitate tissue penetration, the protrusions 322/electrodes 538 may have distal sharpness and strength to penetrate to a predetermined depth of the cavity tissue.

The catheter 22 may be formed of a suitable insulative material, such as silicone, Dacron, ethylene vinyl acetate (EVA), polyimide, polypropylene, Ultem, ceramic, or ABS-type plastics. The catheter 22 preferably has an inner diameter of 0.6 cm to 3.1 cm. The catheter 22 can have a handle (not shown) attached to it proximal end. In the embodiments with the cage electrode structure 303, the amount of overlap between the catheter 22 and the electrode structure 303 can be adjusted and locked at a set length via various mechanisms (ratchet, screw, etc.). The catheter 22 electrically isolates the electrode structure 303 from the skin and subcutaneous tissues.

The length of the electrode structure 303 exposed to tissue is adjusted by moving the catheter 22 with respect to the exposed segment of the electrode structure 303 in order to adjust the length of the long axis and create spherical or ellipsoid geometries.

While specific embodiments have been described above, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes", "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A probe for ablating tissue of a body cavity, comprising:
    a shaft;
    an inflatable balloon connected to a distal end of said shaft, said balloon having an external surface and an internal cavity and being configured to expand within the body cavity, said balloon having a plurality of spaced-apart apertures therethrough which are distributed over the surface;
    a plurality of tubes housed within said internal cavity of said balloon, an end of each said tube being sealed with a respective aperture in said balloon, each said tube defining a passageway with an open distal end disposed at the balloon surface; and
    an electrode mounted within each said tube, said electrodes being translatable along the passageway of the respective tube such that a distal end of each said electrodes can be extended outwardly from said external surface of said balloon to penetrate the tissues of the body cavity and can be retracted inwardly of said external surface of said balloon, said electrodes adapted to transmit electrical energy over the body cavity surface in order to ablate the tissue up to a predetermined depth.

2. The probe of claim 1, further including an insulating cuff between each said electrode and said shaft.

3. The probe of claim 1, wherein said plurality of tubes are mounted within and extend from a central shaft mounted within said internal cavity of said balloon, said central shaft having a closed end and an open end which is sealed to said balloon.

4. The probe of claim 1, wherein each electrode structure is adapted to transmit electrical energy to tissue surrounding the body cavity in order to ablate the tissue up to said predetermined depth when the balloon is expanded.

5. The probe of claim 1, wherein each electrode is formed of at least one of stainless steel, nickel/titanium alloys, copper/zinc alloys, nickel/aluminum alloys, gold, silver, and platinum.

6. The probe of claim 1, wherein said inflatable balloon is made of a nonconducting expandable material.

7. A method of using a probe for ablating tissue of a body cavity, comprising:
    performing a surgical tissue removal to create the body cavity;
    inserting a probe into the body cavity;
    engaging a spherical surface on the probe against tissue of an inner wall of the body cavity;
    advancing a plurality of electrodes distributed over the spherical surface to penetrate the tissue of the inner wall of the body cavity; and
    transmitting electrical energy through said plurality of electrodes to the tissue of the body cavity in order to ablate the tissue over substantially the entire body cavity surface up to a predetermined depth.

8. A method as in claim 7, wherein engaging a spherical surface on the probe against tissue of an inner wall of the body cavity comprises inflating a balloon having a plurality of inner tubes within the body cavity, wherein the tubes each define passages to the spherical surface.

9. A method as in claim 8, wherein individual electrodes of said plurality of electrodes are advanced through each of the passages of the tubes.

10. The method of claim 7, further including inserting a catheter into the body cavity prior to inserting said probe into said body cavity.

* * * * *